US00PP25741P3

(12) United States Plant Patent
Turpin

(10) Patent No.: US PP25,741 P3
(45) Date of Patent: Jul. 28, 2015

(54) PEAR TREE NAMED 'ANP-0118'

(50) Latin Name: *Pyrus communis*
Varietal Denomination: ANP-0118

(71) Applicant: Susanna Turpin, Tatura (AU)

(72) Inventor: Susanna Turpin, Tatura (AU)

( * ) Notice: Subject to any disclaimer, the term of this patent is extended or adjusted under 35 U.S.C. 154(b) by 182 days.

(21) Appl. No.: 13/987,456

(22) Filed: Jul. 25, 2013

(65) Prior Publication Data

US 2015/0033423 P1 Jan. 29, 2015

(51) Int. Cl.
*A01H 5/08* (2006.01)

(52) U.S. Cl.
USPC ..... Plt./176

(58) Field of Classification Search
USPC ..... Plt./176
See application file for complete search history.

*Primary Examiner* — Susan McCormick Ewoldt
(74) *Attorney, Agent, or Firm* — Klarquist Sparkman, LLP

(57) ABSTRACT

A new pear variety distinguished by its small to medium sized fruit which has up to 70% blush coverage; tree ripened, crisp texture and mature for consumption in mid-January (based on harvest in Goulburn Valley, Australia).

6 Drawing Sheets

Latin name of the genus and species of the plant claimed: *Pyrus communis.*

Variety denomination: 'ANP-0118'.

CROSS REFERENCE TO RELATED APPLICATIONS

None

STATEMENT REGARDING FEDERALLY SPONSORED RESEARCH OR DEVELOPMENT

None

BACKGROUND OF THE INVENTION

The present invention relates to a new and distinct variety of pear tree named 'ANP-0118'. My new tree resulted from a planned hybridization program and is a selection from crossing 'Butirra Precoce Morettini' (Unpatented) as the seed parent with 'Corella' (Unpatented) as the pollen parent. The resulting tree was selected when growing in a cultivated area in Goulburn Valley, Australia. The cross was made in 1995 at Stoneville, Western Australia and the population of 434 seedlings established at Tatura, Victoria, Australia. The seedling tree of the 'ANP-0181' variety was selected in 2001 and planted into a replicated trial on 'D6' (not patented) rootstock and 'Quince A' (not patented) rootstock with 'Beurre Hardy' (not patented) pear as an interstock in 2003. Additional trees of the seedling selection were planted at Australian Pome Fruit Improvement Program (APFIP) sites in Western Australia, South Australia and Victoria in the same year for regional evaluation. Further asexual propagation by budding and grafting of trial trees in 2009 and 2012 for large scale evaluation trials at Tatura on 'BP1' rootstock (U.S. Plant Pat. No. 10,231) showed that the foregoing characteristics come true to form, are firmly fixed, and are established and transmitted through succeeding propagations.

BRIEF SUMMARY OF THE INVENTION

The 'ANP-0118' variety is distinguished from other pear varieties due to the following unique combination of characteristics: Fruit are tree ripened with a fine, crisp texture around the harvest period of 'Williams' Bon Chrétien' pear (not patented). The flesh is less juicy than varieties such as 'Doyenne du Comice' and 'Williams' Bon Chrétien'. The fruit are pyriform with a bright red blush over a light green to yellow skin color dependent upon the harvest period. Unlike blushed varieties such as Forelle (not patented) it does not display a 'speckled' red lenticel overcolour.

The new variety was determined to be distinct from the parent varieties 'Butirra Precoce Morettini' and 'Corella' by the following characteristics: The time of beginning of flowering for ANP-0118 is about a week later than 'Corella' whilst its maturity for consumption is before both 'Corella' and 'Butirra Precoce Morettini'. 'ANP-0181' has a distinct fine, crisp flesh that can be eaten directly off the tree whilst both 'Butirra Precoce Morettini' and 'Corella' have typical European pear flesh texture that is hard and dense and requires maturation under cool storage to be consumed.

The following detailed description concerns the original tree, selected on January 2001, and progeny first asexually propagated in 2003. The original tree and progeny have been observed growing in a cultivated area in Goulburn Valley, Australia.

Certain characteristics of this variety may change with changing environmental conditions (such as photoperiod, temperature, moisture, soil conditions, nutrient availability, or other factors). For example, leaf colors may be brighter green if the trees are grown in soil with greater nitrogen concentrations, and may be more yellow when grown in soil containing lesser amounts of nitrogen. Color descriptions and other terminology are used in accordance with their ordinary dictionary descriptions, unless the context clearly indicates otherwise. Color designations (hue/value/chroma) are made with reference to The Royal Horticultural Society Colour Chart (R.H.S.) version 2 published in 1966.

Figure 1:
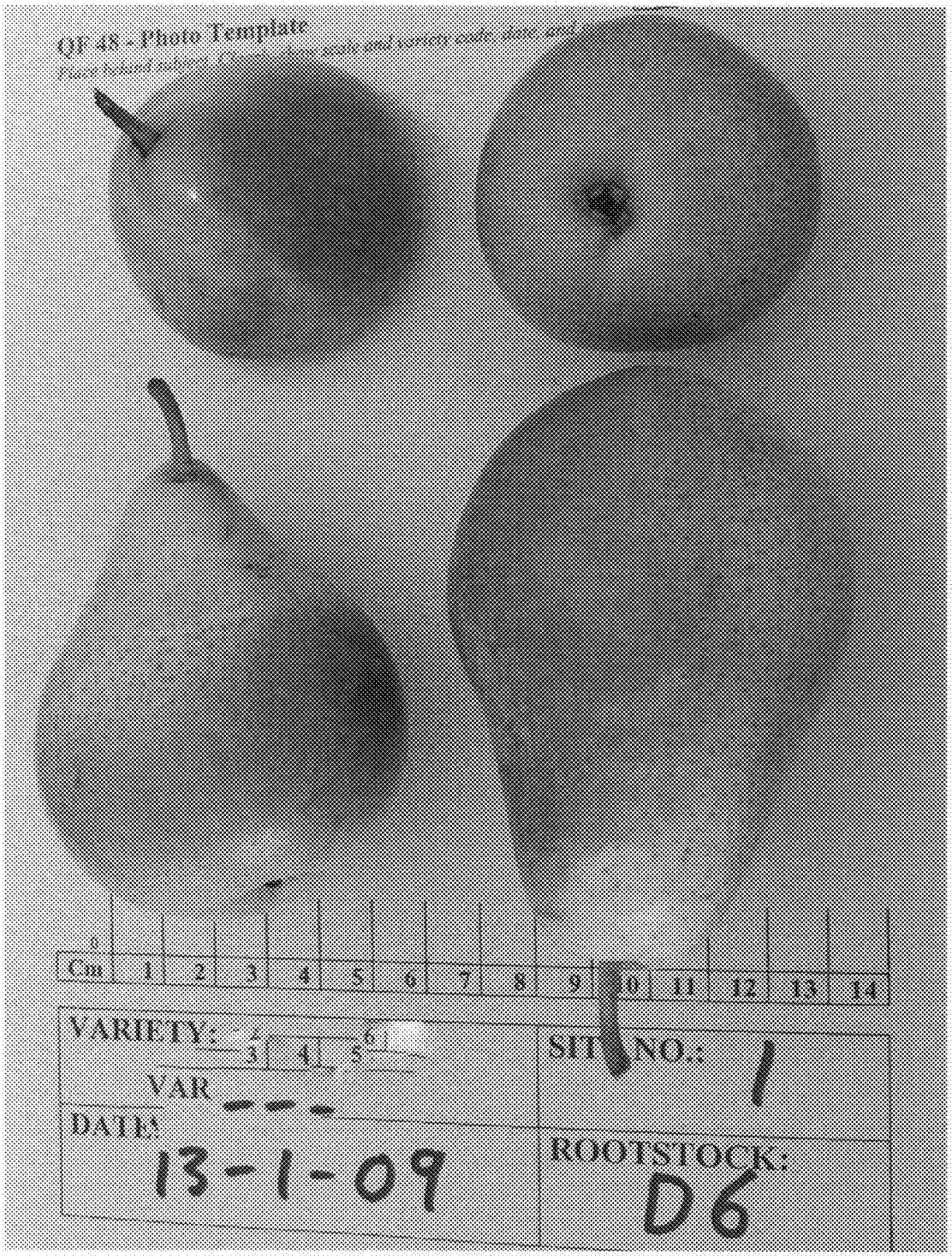
FIG. 1 is a photograph showing the stem end, calyx end and side view of typical fruit of 'ANP-0118'.
Figure 2:
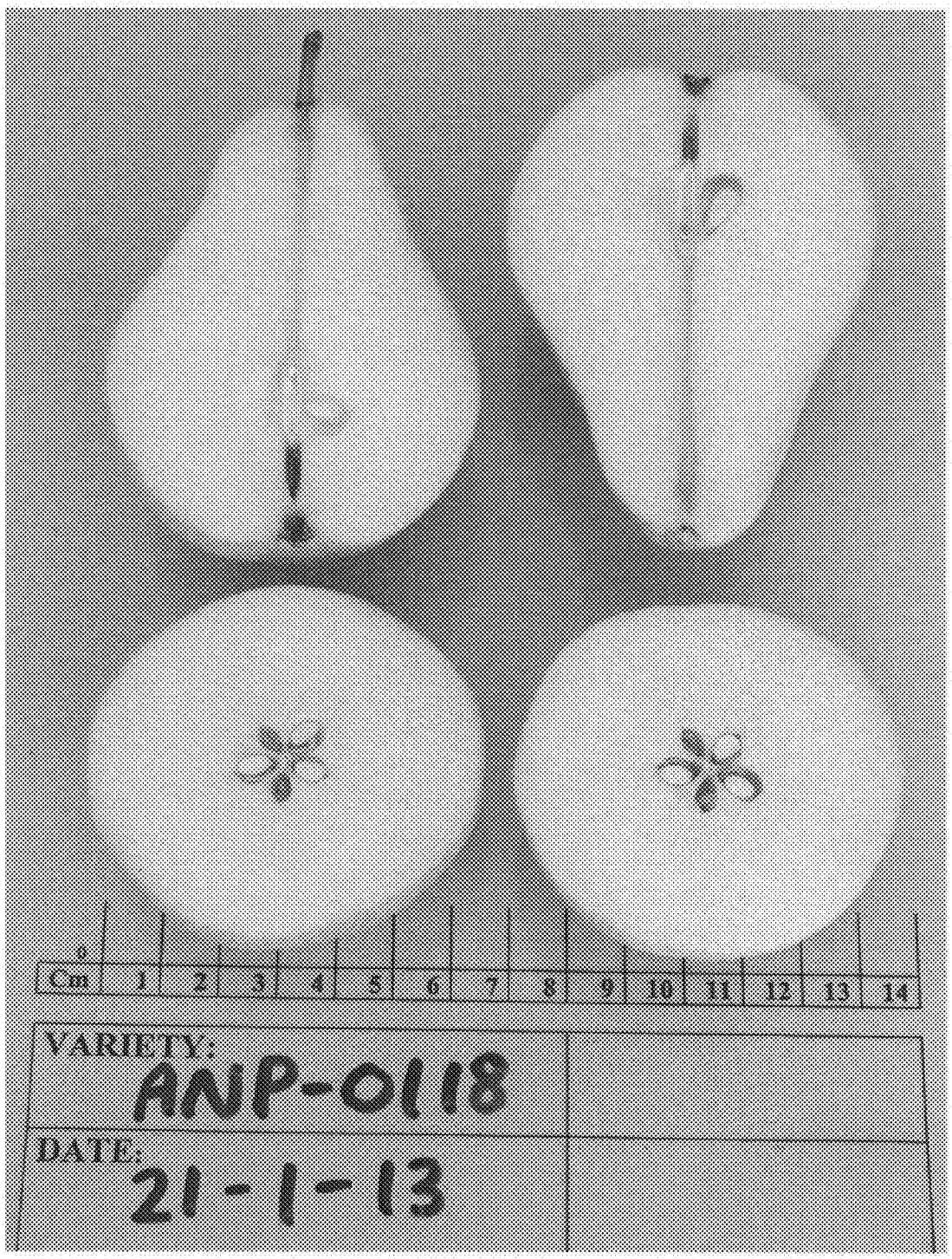
FIG. 2 is a photograph showing the horizontal and vertical cross sectional view of typical fruit of 'ANP-0118'.
Figure 3:
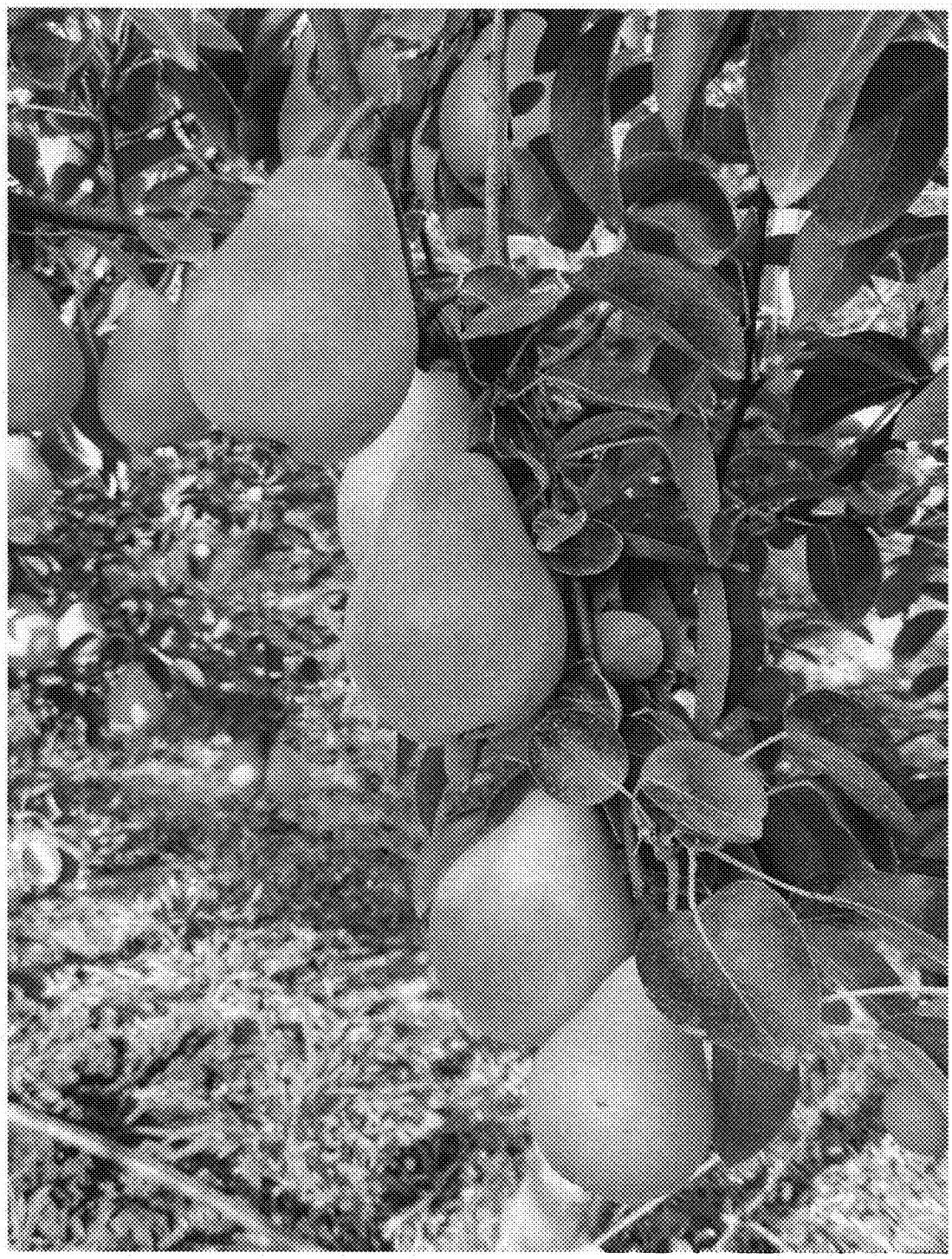
FIG. 3 is a photograph showing typical fruit on a tree of 'ANP-0118'.
Figure 4:
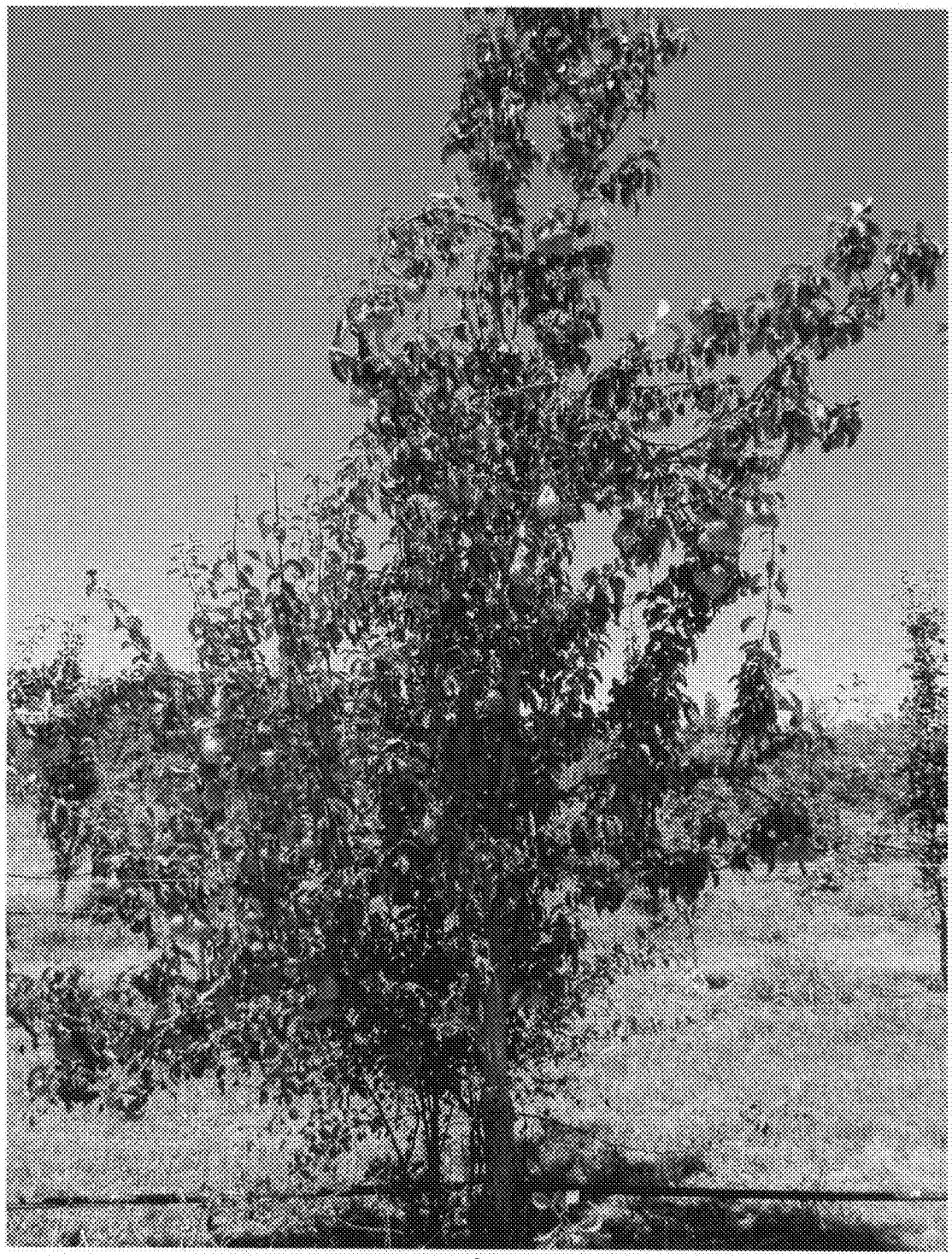
FIG. 4 is a photograph showing a 10 year old tree of 'ANP-0118' on D6 rootstock.
Figure 5:
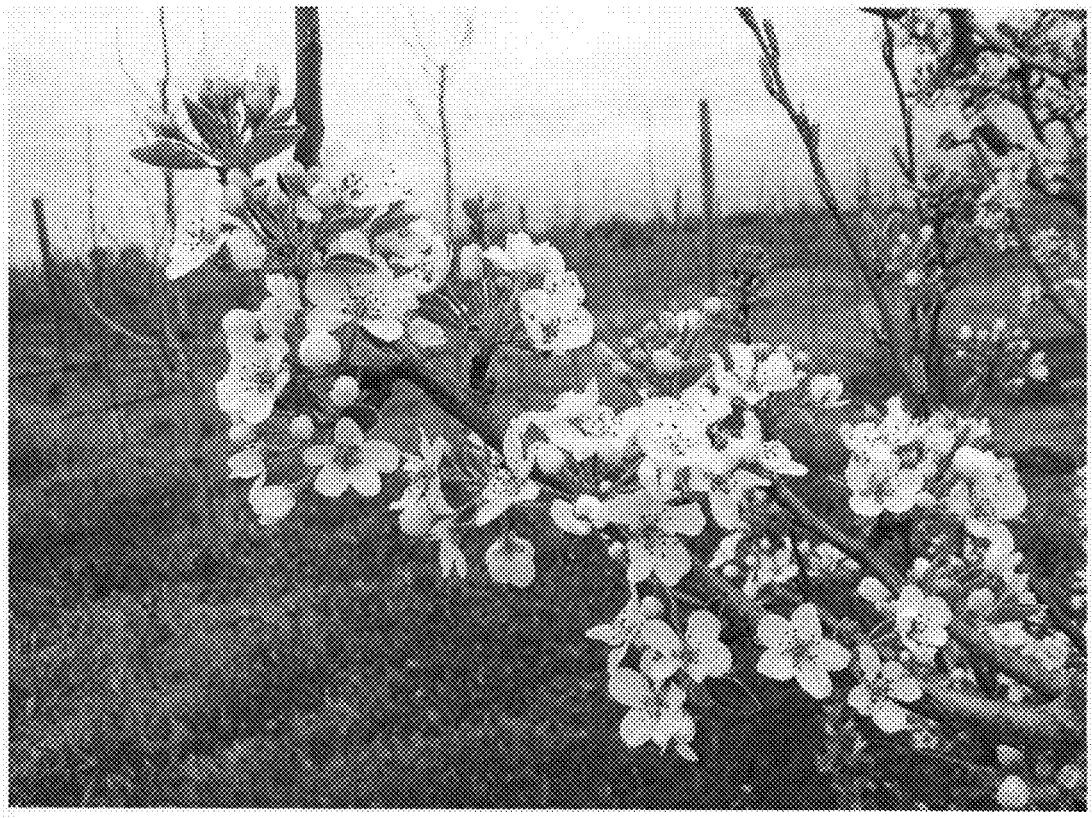
FIG. 5 is a photograph showing a flowering branch of 'ANP-0118'.
Figure 6:
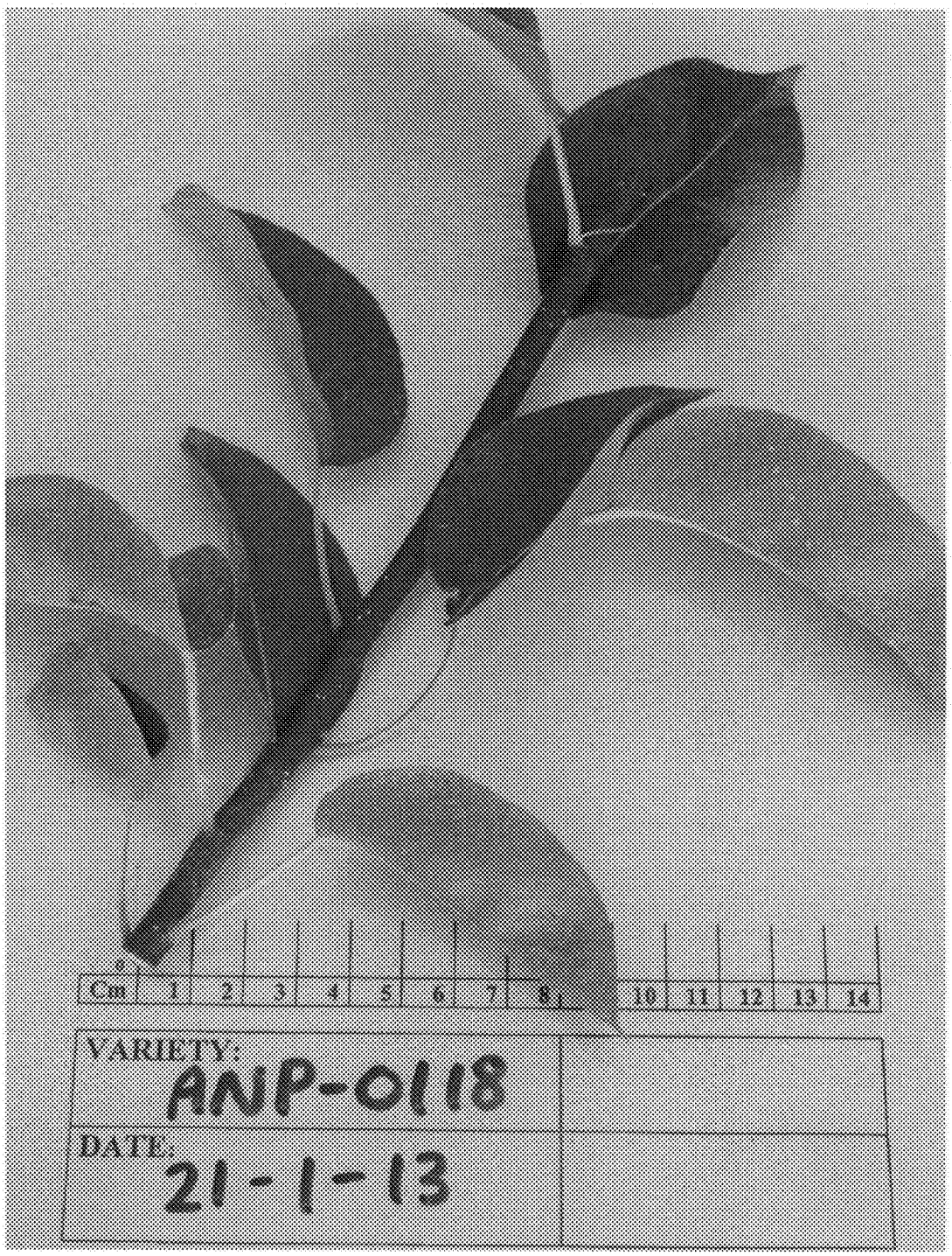
FIG. 6 is a photograph showing the typical mature leaves of 'ANP-0118'.

The color photographs show typical specimens of the leaves and fruit of this new pear tree variety at 10 years old and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photographs alone.

DETAILED DESCRIPTION

Botanical

The following detailed description of the 'ANP-0118' variety is based on observations of asexually reproduced progeny. The observed progeny are trees which were 10 years of age and growing on D6 (*Pyrus calleryana*) variety rootstock in Goulburn Valley, Australia.

Scientific name: *Pyrus communis* 'ANP-0118'.

Parentage:

- *Seed parent*.—'Butirra Precoce Morettini', which resulted from a cross between 'Corsica' and 'Bartlett'.
- *Pollen parent*.—'Corella', a seedling selection of unknown parentage developed by German settlers in the Barossa Valley, South Australia in the late 19th century.

Tree:

- *Vigor*.—Vigorous.
- *Overall shape*.—Tree habit semi-upright.
- *Height*.—Between 3 to 4 m.
- *Width*.—Overall spread of about 1.5 m.
- *Caliper*.—27.2 cm at 20 cm above the graft union.
- *Trunk bark texture*.—Medium, shaggy.
- *Trunk bark color*.—Medium grey (RHS 201C).
- *Patches or other markings*.—Lenticels and bark flakes (Grey-brown RHS 199A).
- *Primary branches*.—Spreading. Angle of emergence from trunk: About 60 degrees.
- *Branch color*.—One year old wood greyed-brown (RHS 199A). Two year old wood greyed-brown (RHS 199B).
- *Branch pubescence*.—None.
- *Branch lenticels*.—Medium density, approximately 8.7 per cm2 (s.d. 2.1), round shape, typically 0.5 to 1.0 mm in diameter; color greyed-brown (RHS 199D).
- *Internodes*.—Average length 2.4 cm (s.d. 0.7) on one year old wood. Average length 2.7 cm (s.d 0.9) on two year old wood.
- *Bearing*.—Annual.
- *Hardiness*.—Average in area tested.
- *Disease resistance*.—No specific testing for relative plant disease resistance has been undertaken. Under observation in 2012 in Goulburn Valley, Australia slight resistance to field infection of pear scab was observed in the leaves and fruit.
- *Pollination*.—Cross compatible with 'Hosui' (not patented), 'Corella' and 'Packhams' Triumph'.

Leaves:

- *Texture*.—Smooth upper and lower surfaces.
- *Sheen*.—Glossy.
- *Length*.—About 40 mm to about 65 mm. Averaging 51.4 mm (s.d. 7.4).
- *Width*.—About 28 mm to about 45 mm. Averaging 34.9 mm (s.d. 4.5).
- *Thickness*.—About 0.15 mm to about 0.24 mm. Averaging 0.19 mm (s.d. 0.02).
- *Petiole*.—About 37 mm (s.d. 8.7) long and about 0.85 mm (s.d. 0.3) in diameter; Yellow-green (RHS 154C) in color.
- *Margin*.—Senate.
- *Tip shape*.—Cuspidate.
- *Stipules*.—Commonly 2 per leaf bud.
- *Leaf color*.—Upper leaf surface: Yellow-green (RHS 146A). Lower leaf surface: Yellow-green (RHS 147B). Vein: Yellow-green (RHS 154D) pinnate with net-like minor veins.
- *Pubescence*.—Upper and lower leaf surfaces weak to absent. The length, width, thickness and other measurements were obtained from observations of 20 typical leaves in Goulburn Valley on 15 Jan. 2013.

Flowers:

- *Size*.—Medium, approximately 27.1 mm in diameter.
- *Shape*.—Ovoid to round.
- *Color*.—Unopened bud: white in color (RHS 155D). Opened flower: white in color (RHS 155D).
- *Petals*.—5 petals per flower; each petal is obovate in shape; about 12.2 mm long and 8.2 mm wide. White in color (RHS 155D).
- *Stamen*.—18 to 20 per flower; each stamen is 5.5 to 7.7 mm long and white in color (RHS 155D). Arranged in a single row.
- *Anthers*.—Red purple (RHS 59B) in color.
- *Pistil*.—Stigma is about 0.1 mm long; rounded at top in shape; 5 styles, and light yellow green (RHS 145B) in color.
- *Sepals*.—About 2.7 mm long and 1.8 mm wide mm wide (at base); Acuminate in shape; yellow green (RHS 144B) in color.
- *Pollen*.—Yellow (RHS 15A) in color.
- *Fragrance*.—Faint.
- *Bloom season*.—15-25 September in Goulburn Valley, Australia; average full bloom date from 2009 to 2012 was 25 September for ANP-0118; 29 September for Packham's Triumph.

Fruit: (Observations from 20 fruit in the 165 to 175 g weight range harvested in Goulburn Valley, Australia).

- *Size*.—Small to medium; About 82 mm long and 62 mm wide to 97 mm long and 68 mm wide.
- *Form*.—Pyriform; globular acute to oblong ovate; symmetric, 1.36 length to diameter ratio.
- *Cavity*.—None; sepals closed.
- *Basin* (*blossom end*).—About 3.3 mm deep and about 16 mm wide.
- *Stem*.—About 17 mm long and 3.4 mm in diameter; yellow-green (RHS 150B) in color; greyed-orange (RHS 163A) overcolour.
- *Locules*.—Small; 5 locules; open.

*Skin*.—Thin with glossy finish; no tendency to become waxy in storage.

*Color*.—General color effect: sun blush; typically 20 to 40% skin coverage and up to 70% skin coverage dependent upon sun exposure. Lenticels slightly conspicuous; small and round; yellow-green in color (RHS 144B). Ground color: Yellow-green (RHS 145B to 150C as fruit ripens). Overcolor: Pinkish red (RHS 45C to 45A dependent upon intensity of blush) with occasional mottling. Russetting: Absent.

*Fruit properties during harvest period in Goulburn Valley, Australia*.—Acid content: about 150 g/100 ml malic acid. Firmness: 4.5 to 6.5 kg for green fruit. Harvested at 5.7 kg (s.d. 0.7) in 2013 and softened about 2 kg after 10 weeks in storage at 0° C. Fruit consumed either crisp off the tree or cool stored for 8-10 weeks to initiate normal softening. Soluble solids: about 11 to 16° brix, average 13.8° brix (s.d. 0.9) at harvest in 2013, and 14.3° brix (s.d. 0.7) after 10 weeks in storage at 0° C. Starch index: on a scale of 1 (100% starch) to 6 (no starch) average 3.2 for green fruit. Flavor: balanced acid/sugar ratio, slight sweetness. Juiciness: medium. Flesh color: white (RHS 155A). Flesh texture: crisp and fine; no grit cells. Aroma: Slight.

*Core*.—Basal bundle area shape about 17.3 cm (s.d. 0.8) long and 20.3 cm (s.d. 2.2) wide; calyx tube semi-closed; core line definition medium.

*Seed*.—Up to 10 seed per fruit, average 5.0 seed (s.d. 2.3) in 2013 and 1 to 2 seed per locule; tear drop shape; about 10.5 mm (s.d. 0.6) long and 5.3 mm (s.d. 0.3) wide; yellow-orange color at harvest (RHS 19C).

*Fruit production*.—Harvest period mid January in Goulburn Valley, Australia. First harvest date 14 Jan. 2013 and last harvest date 21 Jan. 2013. Production per hectare not determined. Trees produce consistent medium crop loads similar to 'Corella'.

*Storage*.—Fruit requires cool storage for 8 to 10 weeks to initiate normal softening. Fruit will then rapidly soften within 2 days at room temperature and requires refrigeration to remain crisp.

*Usage*.—Fresh market.

I claim:

1. A new and distinct variety of pear tree, substantially as herein shown and described.

* * * * *